US005403289A

United States Patent [19]

Berrebi et al.

[11] Patent Number: 5,403,289

[45] Date of Patent: Apr. 4, 1995

[54] AMPOULE WHICH IS TO BE FILLED COMPLETELY AND A SYRINGE FOR USE IN RETAINING OF PHARMACEUTICAL, MEDICAL OR INDUSTRIAL LIQUID PRODUCTS

[75] Inventors: Georges Berrebi, Bourg les Valences; Yves Toporenko, Paris, both of France

[73] Assignee: Societe Cool S.A.R.L., Rhone, France

[21] Appl. No.: 932,535

[22] Filed: Aug. 20, 1992

[30] Foreign Application Priority Data

Aug. 22, 1991 [FR] France ................................ 91 10593

[51] Int. Cl.[6] ................................................ A61M 5/00

[52] U.S. Cl. .................................... 604/232; 604/110; 604/198

[58] Field of Search ......................... 604/232, 194–197, 604/218, 221–222, 231, 82–93, 226, 235, 110, 187; 433/89, 90

[56] References Cited

U.S. PATENT DOCUMENTS

| | | | |
|---|---|---|---|
| 1,456,717 | 5/1923 | Smith et al. | 604/232 |
| 1,718,599 | 6/1929 | Smith | 604/234 |
| 2,147,158 | 2/1939 | Goldenthal | 604/58 |
| 3,811,441 | 5/1974 | Sarnoff | 604/201 |
| 5,000,744 | 3/1991 | Hoffman et al. | 604/232 |
| 5,181,909 | 1/1993 | McFarlane | 604/52 |
| 5,244,465 | 9/1993 | Michel | 604/208 |
| 5,267,961 | 12/1993 | Shaw | 604/110 |

FOREIGN PATENT DOCUMENTS

| | | |
|---|---|---|
| 0082251 | 9/1982 | European Pat. Off. . |
| 460039 | 11/1913 | France . |
| 2016523 | 5/1970 | France . |

OTHER PUBLICATIONS

Two-page French search report.
French application.

*Primary Examiner*—C. Fred Rosenbaum
*Assistant Examiner*—V. Alexander
*Attorney, Agent, or Firm*—Millen, White, Zelano & Branigan

[57] ABSTRACT

An ampoule is filled completely. The ampoule, formed from a casing which may be made of plastic, for example, or made of transparent, opaque or coloured glass, is closed after is has been filled by a frustoconical transverse closure device. The casing of the closure device has a wall provided with an expansion compensator, if the elastic properties of the material used to make this latter are inadequate for complete filling. Filling orifices are provided with a conical raised portion on the outside. Disposed inside the container are hollow spheres which permit the effects of liquid expansion to be compensated for, if necessary, and which are used to make the liquid homogeneous. Caps protect the filling orifices.

3 Claims, 6 Drawing Sheets

AMPOULE WHICH IS TO BE FILLED COMPLETELY AND A SYRINGE FOR USE IN RETAINING OF PHARMACEUTICAL, MEDICAL OR INDUSTRIAL LIQUID PRODUCTS

BACKGROUND OF THE INVENTION

In the present state of the art, the term, "ampoule" is used to denote a cavity filled with liquid in the domains of anatomy, pathology or pharmacy. Pharmaceutical ampoules are flame-sealed glass tubes in which medicinal solutions have been placed beforehand. Ampoules have a number of advantages: exact dosage of product protection of product from oxygen, dirt, indefinite storage if the product is stable, and the possibility of basic sterilisation as far as injectable products are concerned.

Injectable ampoules are one of the best forms of presentation and ways of keeping products for sub-cutaneous and intravenous injections etc. In addition to the usual qualities of ampoules, the glass of which the ampoule is made is said to be neuter, that is to say that it is not capable of reacting on the contents.

Auto-injectable ampoules for very convenient use provide a complete safeguard against asepsis. They are small syringes for use once only and are provided with a needle and are ready to be injected (they are stored in a piece of air-tight plastic material).

Drinkable ampoules are advantageous in that they give an exact dosage and provide good conservation conditions, especially in the case of substances which have been destroyed by oxygen in the air, and sterilisation (but not necessary for drinkable products such as syrups etc.), improves their keeping. Two ampoules containing non-miscible products can be soldered end to end. These are twin ampoules, the contents of which are mixed on use.

The aim of the present invention is to improve the quality of existing ampoules by using a plastics casing which is chemically neuter to the liquids with which it will be in contact. The material used to make the casing can be opaque, transparent, coloured, depending on whether the liquid with which it will be in contact is light-sensitive, in particular sensitive to UV rays.

In accordance with the present invention, a system is provided which includes a syringe combined with an ampoule wherein the syringe has a barrel with first and second ends. A piston with a bore therethrough is positioned in the syringe barrel and a tubular plunger is attached to at first pin thereof to the piston and has a second end thereof projecting from the second end of the syringe barrel. A rod is slidably received through the tubular plunger and the bore of the piston. The rod has a first end projecting from the first end of the barrel and a second end projecting from the second end of the tubular plunger. A closure is provided for closing a first end of the ampoule and there is a coupling between the first end of the rod and the coupling for operating the closure to open and close the first end of the ampoule. A needle is provided at the second end of the ampoule for drawing liquid into the ampoule upon pulling the second end of the plunger after the rod has opened the closure, whereby after the ampoule has been filled with the liquid, the closure is closed to retain a liquid in the ampoule.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION

Figure 1:
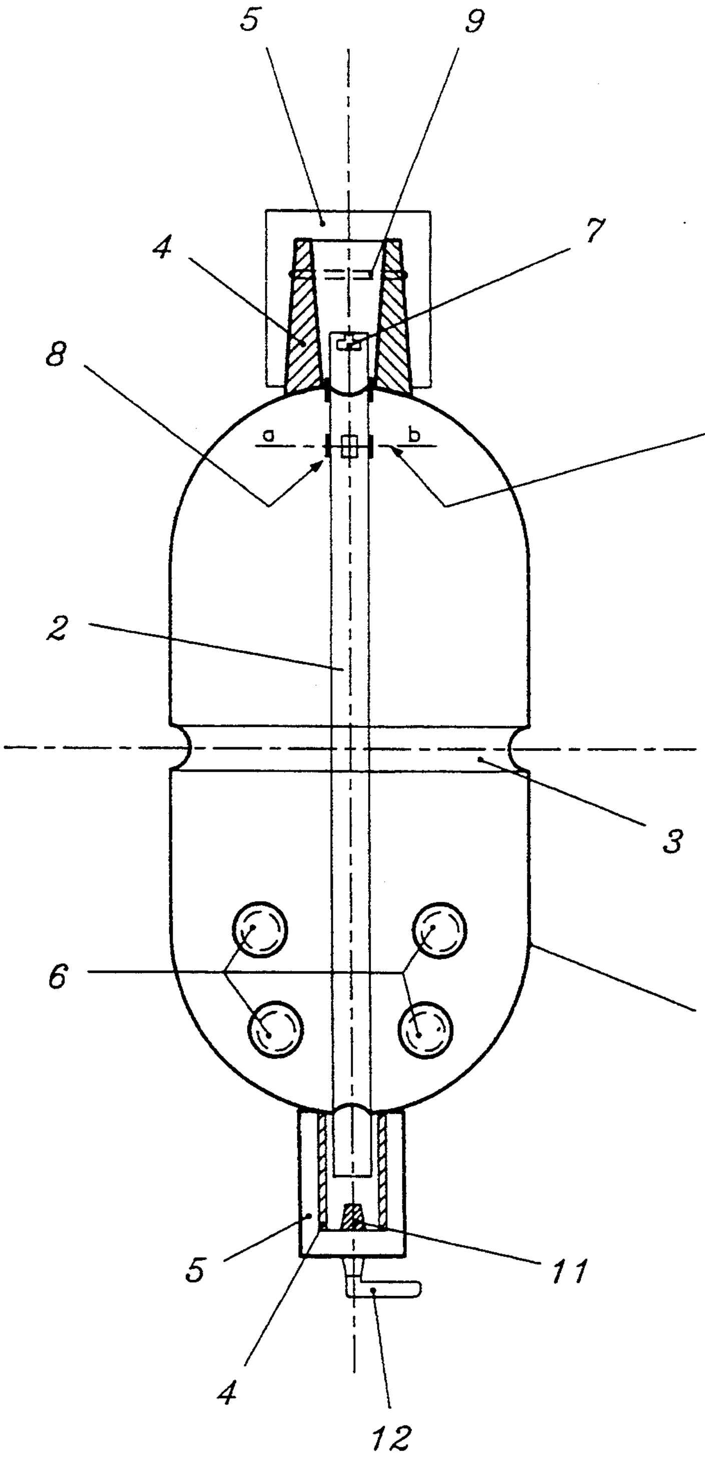
FIG. 1 is a side view of an ampoule, partially in section.

The invention shown in FIG. 1 shows an ampoule, the casing (1) of which is related to a conventional two pointed type glass ampoule, except that the filling orifices are closed mechanically by a transverse shaft (2) of the frustoconical kind required for complete filling. The glass can be replaced by plastic or plexiglass, or metal, or any equivalent material.

The filling orifices are each protected by conical raised portions (4) on the inside and outside; it is seen that the external dimensions and profile of the smallest raised portion enable it to be encased in the largest one, and is favourable towards forming a serial junction between two ampoules, if necessary.

Figure 2:
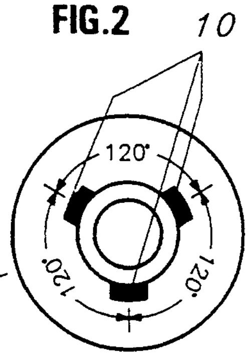
FIG. 2 is a section through the ampoule of FIG. 1 taken on lines a–b.

Each raised portion can accommodate a plug (5) for conical encasement-type closure, or for a snap-shut-type closure with an annular clip (9). If it is recommended that the liquid inside the ampoule be kept homogeneous prior to use, balls or hollow or solid spheres made from a compressible material (6) are introduced into the cavity of the ampoule before the closure shaft is brought into position, (2) they also enable expansion effects caused by positive or negative variations in temperature to be compensated for. The closure shaft (2) is provided with an anti-loss device (8) along the axis a–b (see FIG. 2, shown in section along the axis a–b).

To be more exact, the various elements in FIG. (1) are:

1) An ampoule casing.
2) A closure device, the central part of which is hollowed out.
3) An expansion ring which can be used when designing the ampoule if this latter is to be subject to the effects of temperature.
4) Protection of the filling orifice of the ampoule by a conical raised portion on which the syringe provided for filling and closure purposes is provided. The conical raised portion enables a needle to be used for drainage purposes or a plunger to disengage the closure device when the latter is blocked to be fitted. The plunger can be replaced by a cap which is provided with a needle valve screw, which, when it is under pressure on the closure device, raises it, thereby encouraging the liquid inside the ampoule to flow through a drainage orifice provided in the cap.

5) A protective cap.

6) When the ampoule is designed without an expansion ring, hollow spheres can be used. They also permit homogenisation of the mixture or liquid when the ampoule is agitated.

7) A notch fop bayonet-type extractor.

10) In FIG. 2 (section of closure device along the axis a–b), plugs permitting the closure device to be kept open during the filling operation.

11) A hollow screw.

12) A drawing off tap fitted into the protective cap.

Figure 3:
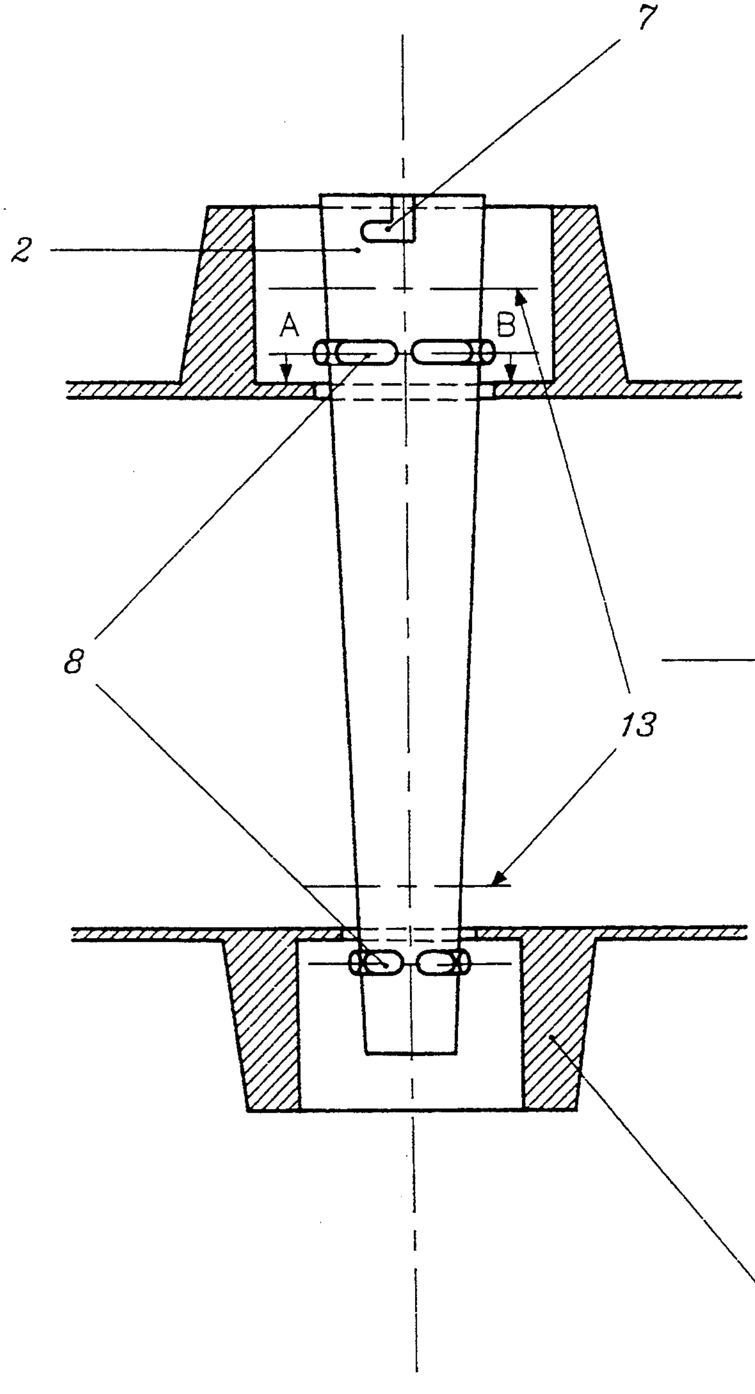
FIG. 3 is a side view, partially in elevation illustrating a frustoconical closure shaft.
Figure 3A:
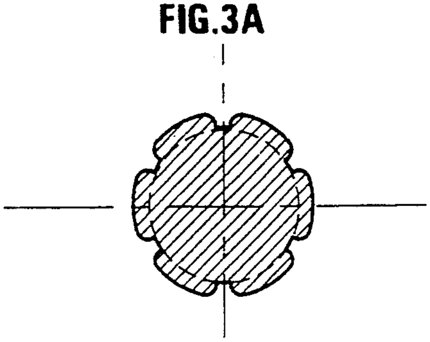

FIG. 3 shows, in detail, the frustoconical closure shaft (2) of plastic material provided with anti-loss devices (8) which hold the closure device in the open position duping the filling operation, the section a–b shows the channels along which the liquid can flow when the ampoule is being filled of emptied. The reference numeral (13) marks the closure planes of the closure shaft, the reference numeral (4) marks the raised portion which is formed in the casing of the ampoule. The reference numeral (7) denotes the bayonet-type extraction device, with which the closure shaft (2) is provided. The raised portions (4) ape designed to accommodate the tip of a syringe or the point of a needle.

Figure 4:
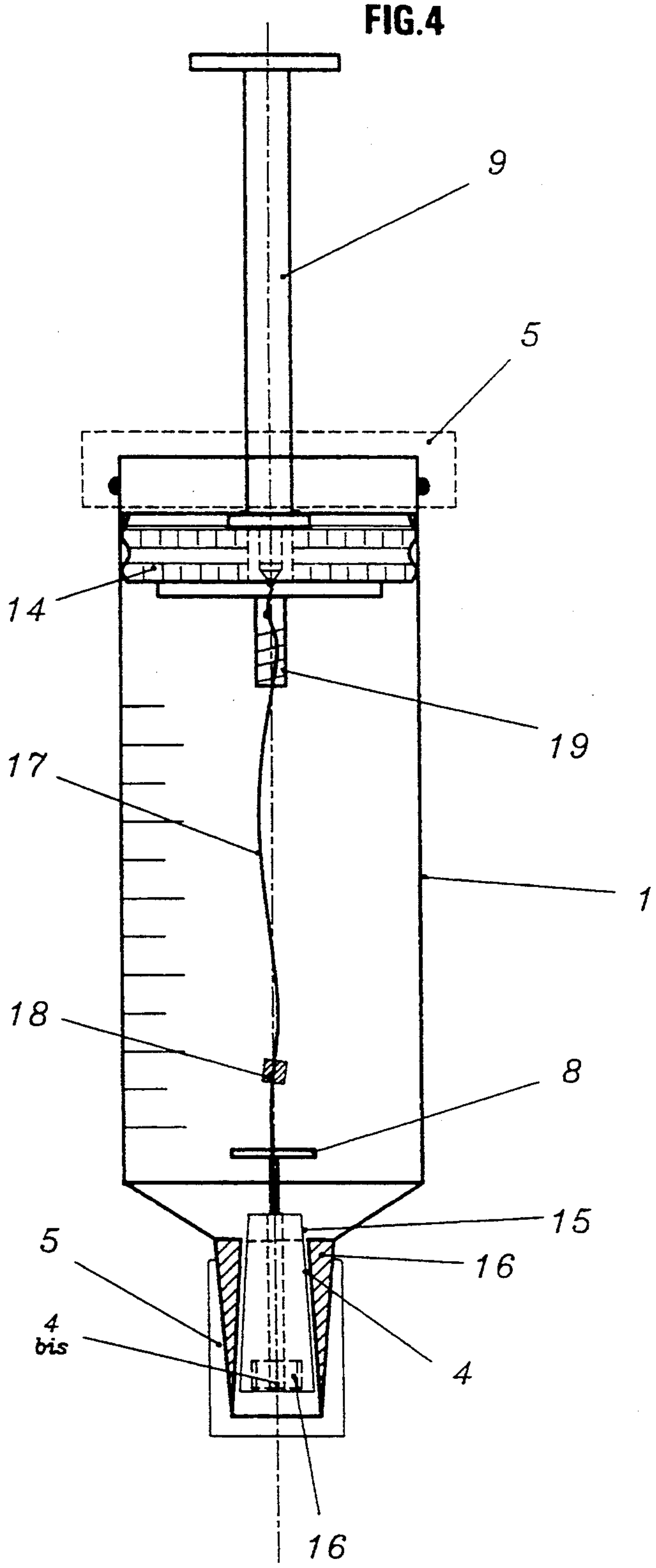
FIG. 4 is a side view of an ampoule configured to carry out the functions of a syringe.

FIG. 4 shows an ampoule which is to be completely filled, which is able to carry out the functions of a syringe. FIG. 4 shows a variant of the ampoule which is to be completely filled and mechanical closure device, designed fop drainage and injection operations and for possible closure operations when the ampoule is being emptied.

The reference numerals correspond to the following designated features:

1) Cylinder made of glass, plastics material, of the like, marked in graduations, and open at the top.

4) Filling orifice with raised portion.

5) Protective cover.

8) Anti-loss device for the closure device.

9) Control rod for piston of the movable type which is able to be fitted to the base of the closure device by screw means or a snap-shut connection.

14) Piston made of plastics material.

15) Frustoconical closure device.

16) Screwthreaded portion or snap-shut closure portion.

17) Flexible mechanical connection by plastic screw between the piston and closure device.

18) Traction pull limiting means.

19) Spindle used to wind up the connecting wire between the piston and closure device when the ampoule is being emptied.

In FIG. 4, the reference numerals are defined as follows:

1) Syringe body or ampoule which is to be completely filled.

4) Conical raised portion permits fitment of a needle for drainage or injection purposes.

4*b*) Flexible tongues used to keep the closure device open when the piston is in the bottom position.

5) Protective cap after the piston control rod has been removed.

8) Anti-loss device.

9) Control rod of piston (movable by unscrewing). Abutment ring or blocks. Filling limit.

14) Plastic or rubber piston.

15) Conical closure device.

16) Screwthreaded portion.

17) Connecting wife between the piston and closure device.

18) Traction compensation means.

Material used for the assembly: Glass or plastics material or equivalent material.

When filled to the limit, the connecting wire (17) between the piston (14) and closure device (15) is stretched, the piston is not in abutment, and the spacing separating the piston from the abutment member is reserved for possible expansion of the liquid.

Figure 5:
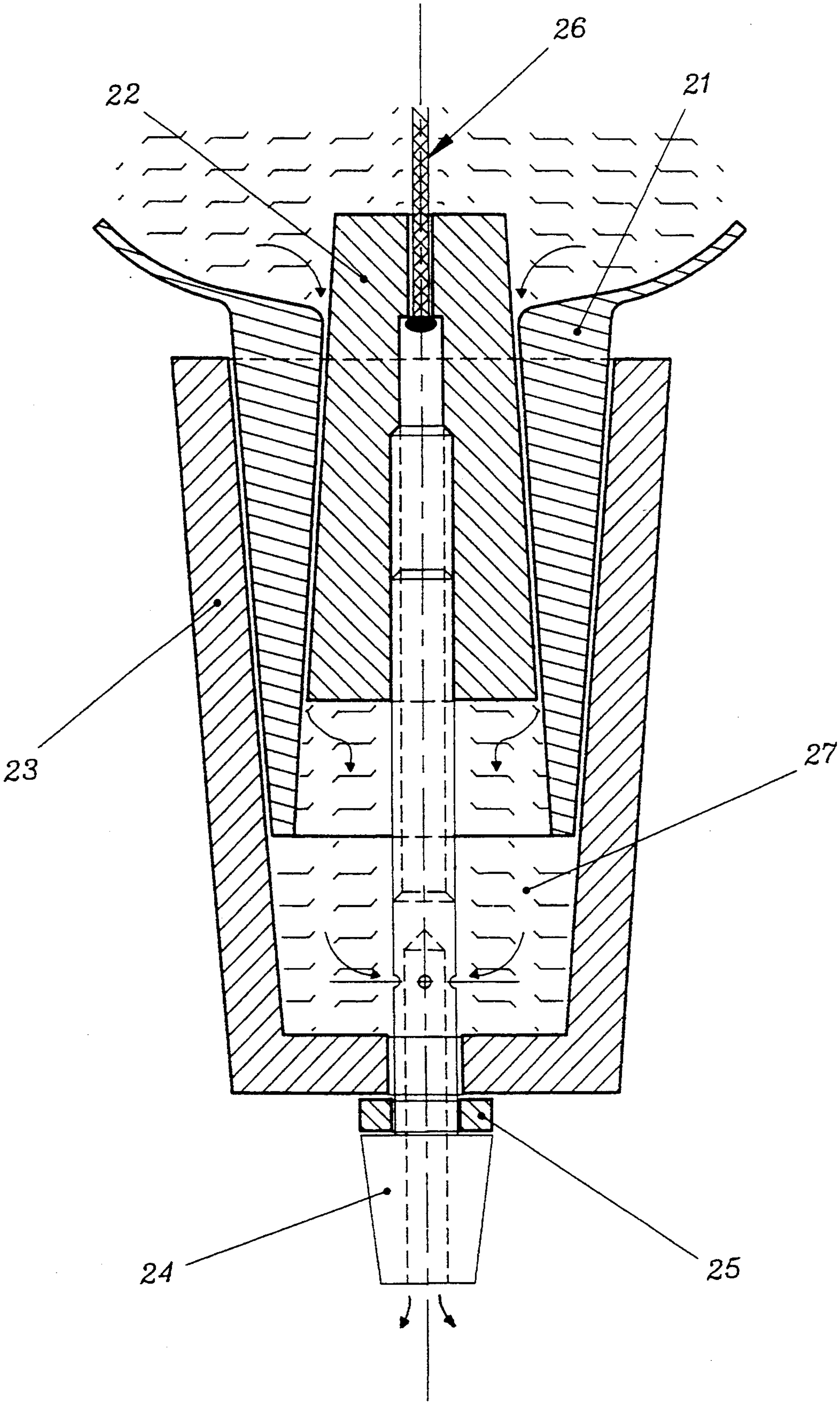
FIG. 5 is the lower end or tip of the ampoule of FIG. 4.

FIG. 5 shows, in detail, the tip of an ampoule which is to be completely filled, defined in FIG. 4, provided with a closure extractor, designed to drain liquid and for the possible use of an injection needle. The reference numerals correspond to the following designated features:

21) Filling orifice of ampoule provided with a conical raised portion.

22) Conical closure device.

23) Supporting cover of extractor.

24) Hollow screw with lateral perforations, and conical tip provided for use with a point of an injection needle.

25) Sealing joint.

26) Connecting wire or cord between closure device and piston.

27) Liquid transfer cavity.

Figure 6:
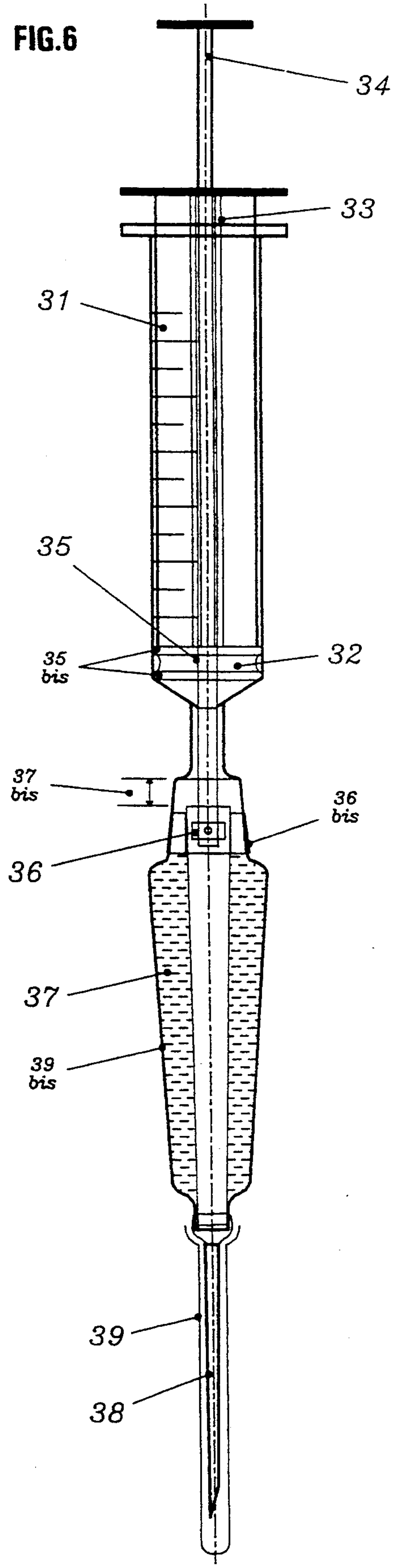
FIG. 6 is a side view of a syringe and ampoule in combination.

FIG. 6 shows the arrangement of an assembly of elements (syringe and ampoule) provided for complete filling. The reference numerals correspond to the Following designated features. FIG. 6 therefore shows an arrangement permitting drainage and injection with an ampoule which is to be completely filled.

31) Syringe body made of plastics material or glass.

32) Piston.

33) Piston control means.

34) Control rod of closure device.

35) Sealing ping for passage of the control means for the closure device.

36) Bayonet-type screwing device.

37) Ampoule body.

38) Drainage needle.

39) Needle protector.

It is possible to distinguish between the following referenced features in FIG. 6:

31) Cylindrical body, marked in graduations.

32) Piston.

33) Hollow rod for controlling displacement of the piston of the syringe.

34) Control rod for closing or opening the closure device of the ampoule.

35) Central sealing ring.

35*b*) Sealing rings of piston.

36) Screw device between the closure device of the ampoule and the control rod of the syringe.

36*b*) Conical junction permitting connection between the syringe body and ampoule body.

37) Liquid.

37*b*) Closure device clearance for ampoule which is to be completely filled.

38) Conical fitting permitting the needle to be joined to the ampoule.

39*b*) Ampoule which is to be completely filled.

39) Needle protector.

FIG. 6 thus shows a dual purpose syringe which is designed for a liquid to be drained or injected by the use of an ampoule which is to be completely filled, this latter being placed between the syringe and the needle.

To satisfy this objective, it is noted that the conventional syringe is modified by the addition of a shaft which moves inside the piston and its control means, and which allows the closure device of the ampoule, intended to contain the liquid which is to be drained or injected, to be acted upon.

Ways of using the syringe and the ampoule which is to be completely filled

The arrangement (syringe, ampoule, needle) is stored in a sterile casing

1. Drainage of liquid (blood, liquid, synovial etc.. ) The various elements are assembled: syringe, ampoule and needle, as shown in the drawings accompanying this description. After assembling it with one hand, the other hand holds the assembly by the control rod for closing or opening the closure device of the ampoule, and this rod is pushed until it is clutched inside the bayonet-type device of the closure device of the ampoule. The closure device is unscrewed from the ampoule, and the ampoule is opened by slightly rotating and pulling the control rod of the syringe which is kept for this movement.

Once the orifices of the ampoule are cleared, and with the piston of the syringe at zero, the needle is pushed into the drainage zone, and filling of the ampoule commences by displacing the piston of the syringe. Once the liquid is seen to appear at the closure device clearance limit, through the syringe element which forms the junction with the ampoule, it is confirmed that filling has been completed. When the control rod of the closure device is pushed down, it causes this latter to slide inside the ampoule and causes the orifices thereof to close, rotation in the opposite direction of the control rod locking the closure device and enabling the control rod to be disengaged. The assembly is dismantled with the customary precautions (putting on the needle protector, taking off the ampoule from the syringe or intermediate connecting element). Preferably, protective caps ape also put on the filling orifices of the ampoule.

2. Use of the ampoule, which is to be completely filled, for injection purposes

The protective caps of the ampoule, which is assumed as being sterilised, are removed, the main orifice which acts as a filling means is engaged over the conical Fitting at the junction of the syringe by the intermediary of the closure device control means provided on the syringe. The closure device is then unscrewed From the ampoule, and the orifices are opened by pulling on the closure device control means provided on the syringe. The syringe body is then filled by displacement of the piston. The empty ampoule is removed from the assembly and replaced by a needle. The injection is then given, observing current deontology.

The advantages of this system are:

Complete filling of an ampoule and closing it so that it is perfectly sealed, the filling orifices of the ampoule being able to be provided additionally with sealing covers of a film which can be stripped off by using a Fast polymerisation glue.

No heat source intervenes in the closure operation of the ampoule, complete filling excludes any presence of air or gas which risks altering of oxidising the liquid of mixture to be protected.

The process avoids handling which promotes microbic production, in bacteriology and cytology, in particular, due to the complicated and delicate transfers.

Areas of Application of the System:

Medical (blood analysis, synovia drainage, pleural, etc.).

Pharmaceutical (conservation of serum, vaccines, sensitive liquid products)

Biology, artificial insemination etc.

Chemical industries, specialised research through liquid drainage etc.

In essence, the combination of syringe and ampoule (39*b*) shown in FIG. 6 utilizes a syringe barrel (31) having a first end and a second end. A piston (32) is positioned in the syringe barrel. The piston has a bore (35) therethrough. A tubular plunger (33) has a first end attached to the piston (32) and a second end projecting from the second end of the barrel (31). A rod (34) is slidably received through the tubular plunger (33) and the bore (34) in the piston. The rod (34) has a first end projecting from the first end of the barrel (31) (or in the drawing from the bottom end of the barrel) and a second end projecting from the second of the tubular plunger (33). A closure (37*b*) closes the first end of the ampoule (39*b*) and a coupling (36) connects the first end of the rod to the closure (37*b*) for operating the closure to open and close the first end of the ampoule (39). A needle (38) is positioned at the second end of the ampoule (39*b*) for drawing liquid into the ampoule upon pulling the second end of the plunger (33) after the rod (34) has opened the closure (37*b*). Accordingly, after the ampoule (39*b*) has been filled with the liquid (37), the closure is closed to retain the liquid in the ampoule. The coupling (36) connecting the closure (37*b*) to the rod is a screw coupling which, when rotated by the rod, opens and closes the closure. As is seen in FIG. 6, there is a space (37*b*) which provides closure device clearance for the ampoule so that the ampoule can be completely filled.

Figure 7:
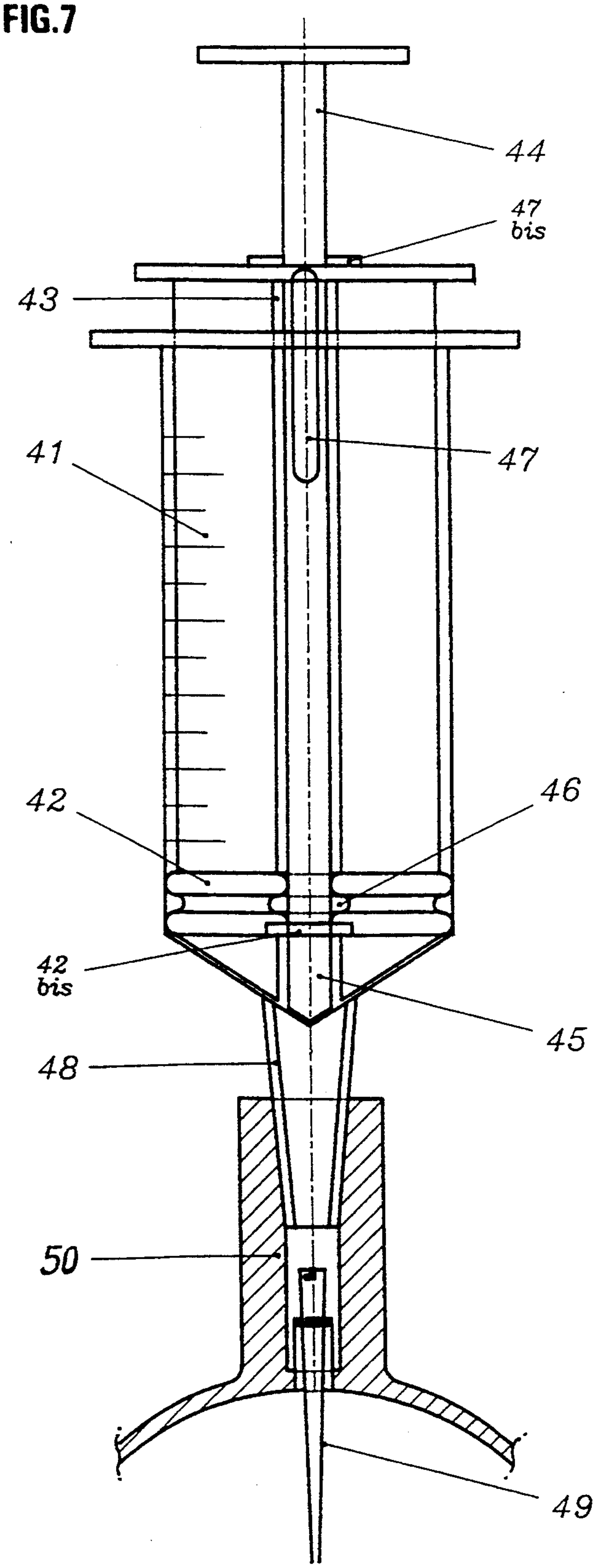
FIG. 7 is a side view of a dual purpose syringe permitting drainage and injections from an ampoule which is to be completely filled.

FIG. 7 shows a dual purpose syringe permitting drainages and injections from an ampoule which is to be completely filled.

FIG. 7 shows a syringe designed for use with ampoules which are to be completely filled when the syringe body is to be drained or emptied in order to give an injection. The reference numerals correspond to the following designated features:

41) Syringe body.
42) Piston.
43) Piston control means.
44) Control rod of closure device of ampoule.
45) Tip of control rod fitted to the system provided on the key for closing the ampoule.
46) Sealing ring for passage of the piston through the control rod of the closure device.
47) Clearance limit of control means of closure device.
48) Conical fitting for use on ampoule.
49) Closure device of ampoule.
50) Raised portion of ampoule.

In FIG. 7 which illustrates a dual purpose syringe permitting drainage and injection from an ampoule which is to be completely filled, the reference numerals, in greater detail, denote the following:

41) A cylindrical body marked in graduations.
42) Piston of the syringe.
42*b*) Abutment.
43) Hollow rod for controlling displacement of the piston of the syringe.

44) Control rod for opening or closing the closure device of the ampoule which is to be completely filled.
45) Contact needle of the control means of the closure device which can be provided on the system incorporating the ampoule which is to be completely filled.
46) A sealing ring of traversing form for the piston.
47*b*) A key for immobilising the control rod for opening the closure device, fixing it to the control means of the piston.
47) A slider for the key for immobilising the control rod of the closure device.
48) Central, conical junction fitted to the filling orifice of the ampoule, permitting a possible connection to be made with a needle.
49) Closure device of the ampoule.
50) Ampoule to be completely filled, in the open position.

The invention is thus concerned with several systems deriving from the same idea in particular a system wherein a syringe designed for drainage or injection purposes is fitted to an ampoule made of plastics material, glass, metal or any similar material. The ampoule is the type which is to be filled completely and being provided with a conical closure device (usually excluding any heat). The system being characterised (see FIGS. 4 to 7) by the installation of a control rod for the closure device which moves inside the rod or the control device of the piston of the syringe with various systems in isolation or in combination. Namely the system is characterised by the use of a control means for the closure device whose screw key glides in the depth of the piston of the syringe. The system being further characterised by the use of a sealing ring ((46) in FIG. 7) disposed inside the syringe piston which permits passage of the control shaft of the closure device of the ampoule which is to be completely filled. The system is further characterised by the use of a device which ensures perfect sealing and easy displacement of the control shaft of the closure device of the ampoule which is to be completely filled. The system is also characterised by an adjoining device which extends the body, marked in graduations, of the syringe (a device which has been moulded, or the like) which permits an injection needle to be fitted, or for an ampoule which is to be completely filled to be placed between the syringe and needle. The control means of the ampoule is provided for the purpose of opening the closure device, being limited in respect of its clearance. The system is characterised by a syringe tip which permits fitment of an ampoule which is to be completely filled for drainage purposes, and of a needle for injection purposes. The system uses a control rod for the closure device of the ampoule which is to be completely filled, the end of the rod having a snap-shut closure device which is fitted to the closure device provided on the ampoule for which the syringe is designed. The system further uses a control rod, which, by virtue of its single or double bayonet-type tip, makes it possible for the closure device of an ampoule which is to be completely filled to be handled (screwed, unscrewed, pulled, pushed). The system is characterised by the use of plastic material or glass or metal with the intention of making visible certain parts of the syringe which are indispensable for its use (filling level of syringe and ampoule), and of making the control means of the closure device visible. The system is further characterised by the possibility of having a flap disposed on the piston of the syringe permitting the syringe to be used basically as a suction pump.

When the invention is more particularly concerned with an ampoule which is to be completely filled (FIGS. 1 and 2), the ampoule is characterised by the use of a casing (1) of transparent or nontransparent plastics material, coloured in appropriate shades in order to protect it from certain light rays, metallised under vacuum, possibly when the liquid which it is to contain has to be sheltered from the light, (therefore, in this case, an opaque-rendering operation is undertaken by metallisation under vacuum). The ampoule is also characterised in that it is designed to be of a shape which is selected, in particular, from the group constituted of cylinders, spheres, parallelepipeds, most frequently produced with a cylindrical ferrule to which hemispherical ends are joined, which are provided at the vertices thereof with calibrated openings which vary in diameter in each case. The design of the configuration or assembly means that the calibrated openings disposed at the vertices of the hemispherical cups are disposed on an axis which can, if necessary, be different from the axis of symmetry of the casing forming the ampoule.

The ampoule is preferably characterised by having, fitted into its casing, a circular swelling or flange which permits an increase in its volume when the liquid contained therein expands due to congelation or due to an increase in temperature of the liquid (caused by complete filling).

The ampoule in FIG. 1 is also characterised by complete filling being obtained when a depression is formed by using a syringe fitted to it, as shown in FIG. 4 or 5, or by immersing the ampoule in the liquid which it is to contain, or by filling it at source; in each of these cases, the closure device is in the open position, and is then slid into the opening orifices of the ampoule when complete filling has been noted.

The ampoule, in isolation or in combination with the syringe fitted to it, can also be characterised by:

- use of a mechanical closure device in the form of a conical pin which slides mechanically by means of a fitted syringe or by means of a Fitted filling machine.
- use of conical closure devices (FIG. 2) in the form of one single element which traverses the ampoule, or in the form of one conical element per orifice (two per ampoule).
- use of a conical traversing type of closure device, the centre of which can be compressed in order compensate for expansion of the liquid contained in the ampoule due to the effects of heat or cold.
- the design of the filling orifices and use of one or two frustoconical closure devices which provide perfect closure due to the effects of compression produced when a selected conical element engages in a circular orifice well adapted to it.
- design of the casing whose filling orifices are protected by a frustoconical annular shaft on the outside provided with a bayonet-type screw device kept for the closure device, the frustoconical shape of the shaft or raised portion (4) facilitating fitment of said syringe fitted to the ampoule (and also of the needle to the ampoule when liquid is being drained). The raised portions disposed around the filling orifices of the ampoule enable removable protective covers, or protective covers which can be peeled off, to be put in place use of a semi-rigid plastics basing.

non-fragility of the elements of which it is composed.

design of a casing with two conical filling orifices, closed by a conical pin.

the possible use of hollow balls or spheres ((6) in FIG. 1) made of a resilient plastics material to permit compensation for liquid expansion due to the effects of temperature, and also promoting homogenisation of the liquid when the ampoule is agitated.

use of a conical pin-shaped closure device, wherein provided in the length not used to close the ampoule, and between the two filling orifices, a slight distance away from them ape three flexible plugs (FIG. 2 (10)) disposed at 120° C. along a median plane perpendicular to the shaft of the closure device, and which enable the closure device to be kept in a position where it is disengaged from the orifices, in order to facilitate filling of the ampoule.

use of protective covers or caps (5) which are placed over the shafts or raised portions (4) which protect the filling orifices of the ampoule, and some of which are provided with clips or a sealing device in order to ensure that the system is inviolable after it has been filled.

use of a cover or a cap which is placed over the narrowest orifice of the ampoule by lifting the closure device, which encourages flow of the liquid inside, communicating it with a drainage orifice controlled by the same screw.

use of a hollowed out closure device, the central part of which in contact with the liquid can act as a means for compensating for expansion if the ampoule is not provided with one such means, and which can prevent destruction of the ampoule due to liquid expansion caused by the effects of temperatures greater than or less than ° C.

As indicated hereinabove, the invention also relates to a system consisting of a syringe combined with the ampoule for complete filling. The system is characterised by its design which makes it possible for it to be both an ampoule for complete filling and a syringe at one and the same time.

The system is characterised, see in particular FIG. 4 of the syringe, by use of a cylindrical body (1) marked in mml or in $cm^3$ and made of glass, metal or more usually of a plastics material which is entirely or partially translucent, transparent or coloured, and the material of which is selected depending on the liquid which it is to contain, and characterised by the use of a piston (14) made of rubber, glass, plastics material, wedged between two plates or rigid jaws, the central assembly part of which is provided with a screw pitch on which a control rod (9) is secured which can be moved by unscrewing or by snap connection means. In addition, the system can be characterised by the use of a flexible wire (17) (nylon, steel, etc.) which forms a connection or a coupling between the base of the piston and the closure device (15) placed at the base of the cylinder, in an outlet tube which is especially designed for this purpose, and which enables the excess wife to be wound up, particularly when the piston is adjacent to the closure device. Displacing a piston creates the depression needed to fill the cylinder, and when it has completed its travel the connection coupling the piston and the closure device is tensioned, thereby bringing the closure device to its closure point and imprisoning the liquid sucked in within the volume defined by the cylinder, the capacity of which is limited by the piston and closure device. It is possible to use a traction compensation means (18) which is disposed on the wife (17) coupling the piston and the closure device, or a wire with an elastic limit which corresponds to a piston stop which is placed beyond the usual clearance of this latter, and the displacement of which is the same as the upper filling limit, a safety cap or cover being snapped on, or engaged like an seated capsule which can be torn off or peeled off after the control rod of the pistion has been taken apart.

The system is also characterised by the use of an anti-loss device (8) which extends the system and keeps it in the outlet tube for which it is provided, with, in addition, use of a conical closure device (15), the large base of which can accommodate three flexible tongue portions (4*b*) disposed at 120° C., the ends of these latter bearing against a circular groove formed in the raised portion which protects the filling orifice, and holding the closure device open during the filling cycle of the ampoule or syringe.

The system is also preferably characterised (FIG. (5)) by the use of a connecting thread or member (26) between the piston and closure device (22) which is wound up in a space provided between the bottom part of the piston and the closure device, further characterised by use of a outlet tube disposed axially at the base of the cylinder and which acts as a filling and emptying orifice and which is protected by a frustoconical annular shaft on the outside; the shaft or raised portion is designed for an ampoule or a needle used for drainage or injection purposes to be fitted thereto; it can also receive a cover or a cap which is provided with a clip for sealing in order to guarantee that the system is inviolable after it has been filled. In accordance with various alternative embodiments, the system can also be characterised by use of a closure device made of plastics material or rubber, and the length by which it exceeds the outlet tube which acts as its seat enables blockages to be eliminated; a threaded cavity enables an extractor or the control rod of the piston to be screwed on in order to unblock the closure device if necessary; a portion which can be pushed down by a needle can also be provided, and the connection between the piston and the closure device is linked to the anti-loss configuration.

Finally, the system can be characterized by use of a cylinder which is open at the top and which enables the piston and the various syringe elements to be assembled, and characterised by the possible use of a shaft or spindle which is fixed to the base of the piston, on which the connecting wire between the piston and the closure device is secured, and which is used to remount the closure device by tensioning of the wire when the piston is rotated.

We claim:

1. A system in which a syringe is fillable with liquid from an ampoule wherein the syringe comprises:

a tubular body having a first end with an opening therein for drawing liquid into the body from an ampoule and for attaching an injector needle and having a second end with a second opening therethrough;

a piston within the tubular body, the piston having a piston rod attached thereto, the piston rod extending through the opening in the second end of the tubular body and having a tether winding portion thereon extending past the piston;

a flexible wire tether attached at one end to the piston at a first end thereof and being wound around the tether winding portion of the piston rod when the piston rod is proximate the first end of the tube;

a conical stopper within the opening at the first end of the tubular body, the conical stopper having the flexible wire tether attached thereto at a second end of the wire tether; and a traction compensating means on the wire tether, the traction compensating means having an elastic limit corresponding to a piston stop point beyond normal clearance of the piston allowing the displacement of the piston to be equivalent to an upper filling limit of the tubular body, wherein as the tether is tensioned the conical stopper seats within the opening in the first end of the tubular body closing the tubular body and retaining the liquid therein.

2. The system according to claim 1 further including an outlet tube defining the opening at the first end of the tubular body, the outlet tube having a frustoconical outer surface for receiving a needle thereon for use in drainage or injection and for receiving a protective cap.

3. A system in which a syringe is used with an ampoule to retain liquid wherein the syringe comprises:

a tubular body having a first end with an opening therein for drawing liquid into the body from an ampoule and for attaching an injector needle and having a second end with a second opening therethrough;

a piston within the tubular body, the piston having a piston rod attached thereto, the piston rod extending through the opening in the second end of the tubular body and having a tether winding portion extending past the piston;

a flexible wire tether attached at one end to the piston at a first end thereof and being wound around the tether winding portion of the piston rod when the piston rod is proximate the first end of the tube;

a conical stopper within in the opening at the first end of the tubular body, the conical stopper having the flexible wire tether attached thereto at a second end of the wire tether;

wherein as the tether is tensioned the conical stopper seats within the opening in the first end of the tubular body closing the tubular body and retaining the liquid therein; and an outlet tube defining the opening at the first end of the tubular body, the outlet tube having a frustoconical outer surface for receiving a needle thereon for use in drainage or injection and for receiving a protective cap.

* * * * *